United States Patent [19]

Igushi et al.

[11] Patent Number: 5,164,787
[45] Date of Patent: Nov. 17, 1992

[54] APPARATUS FOR MEASURING PARTICLE SIZE DISTRIBUTION

[75] Inventors: Tatsuo Igushi; Yoshiaki Togawa, both of Kyoto, Japan

[73] Assignee: Horiba, Ltd., Kyoto, Japan

[21] Appl. No.: 786,525

[22] Filed: Nov. 1, 1991

[30] Foreign Application Priority Data

Nov. 17, 1990 [JP] Japan .................................. 2-120547

[51] Int. Cl.⁵ ............................................ G01N 15/02
[52] U.S. Cl. ..................................... 356/336; 356/343
[58] Field of Search ....................... 356/336, 338, 343; 250/574

[56] References Cited

U.S. PATENT DOCUMENTS 4,679,939  7/1987  Curry et al. .......................... 356/336
4,781,460  11/1988  Bott ..................................... 356/338
5,105,093  4/1992  Niwa ................................... 250/574

FOREIGN PATENT DOCUMENTS 115950  5/1991  Japan .................................. 356/336

Primary Examiner—Richard A. Rosenberger
Attorney, Agent, or Firm—Price, Gess & Ubell

[57] ABSTRACT

A particular size measuring apparatus uses laser light and monochrome beams of different wavelengths to measure a wide range of particle sizes. The monochrome beams are obtained from a lamp source and are changed in wavelength by a group of band-pass filters, whereby different ranges of particle sizes can be measured for the respective single wavelengths and thus the range of particle sizes capable of being measured can be expanded.

11 Claims, 3 Drawing Sheets

APPARATUS FOR MEASURING PARTICLE SIZE DISTRIBUTION

BACKGROUND OF THE INVENTION

1. Field of the Invention

The present invention relates to an apparatus for measuring particles size distribution in which the particle size distribution of sample particles is measured by utilizing a diffracting phenomenon or a scattering phenomenon brought about by irradiating dispersed particles with a light.

2. Description of Related Art

In an apparatus for measuring a particle size distribution by utilizing a diffracting phenomenon or a scattering phenomenon of light by particles, the intensity distribution of the diffracted light or scattered light is used. In such a measurement, a relationship between a diffracted angle or a scattered angle and an optical intensity is measured and the output signals are subjected to an operation based on a theory of Fraunhofer diffraction or Mie scattering to calculate the particle size distribution of the sample particles.

FIG. 5 is a diagram showing a measuring optical system of a conventional apparatus for measuring a particle size distribution. A sample cell 1 is a transparent vessel, in which a medium with sample particles dispersed therein is housed. The sample cell 1 is irradiated with parallel laser beams L from an optical system 3 composed of a laser beam source 2 and the like.

The laser beams L, diffracted or scattered, by sample particles within the sample cell 1, are received by a ring-shaped detector 5 through one of the collecting lenses 4a, 4b, 4c, which are selected to determine the particle size distribution of the sample particles from a measured optical intensity distribution of the laser beams L.

In the above-described apparatus, in order to focus the diffracted or scattered laser beams L into an image on the ring-like detector 5, a plurality of condenser lenses 4a, 4b, 4c, each different in focal distance, are provided. In a measurement of sample particles having smaller particle diameters exhibiting larger scattering angles, the condenser lens 4a having a short focal distance (f1) is used while the ring-shaped detector 5 is also shifted to a position farther from the condenser lens 4a. On the contrary, in the case where sample particles having larger particle diameters exhibiting smaller scattering angles, the condenser lens 4c having a long focal distance (f3) is used while the ring-shaped detector 5 is also shifted to a position close to the condensed lens 4c.

A plurality of condenser lenses 4a, 4b, 4c, different in focal distance, are exchangedly used in the above-described manner, so that the particles size distribution can be measured over a wide range of particle sizes, as shown in FIG. 6.

Referring to FIG. 6, a range A of particle sizes having smaller particle diameters is measured by the use of the condensed lens 4a having a short focal distance (f1), a range B of particle sizes having particle diameters larger than those of range A is measured by the use of the condenser lens 4b having a slightly longer focal distance (f2), and a range C of particle sizes having still larger particle diameters is measured by the used of the condenser lens 4c having a still longer focal distance (f3). respectively.

The above conventional apparatus for measuring a particle size distribution requires a construction so that the respective condenser lenses 4a, 4b, 4c are changed for each range of particle sizes corresponding to the respective condenser lenses 4a, 4b. 4c. Additionally, the ring-shaped detector 5 is shifted as occasion demands, for each individual range of particle sizes to conduct the measurement. A problem has occurred when the sample particles extend over a plurality of ranges of particle sizes because the optical system must be changed many times, and thus the particle size distribution may not be accurately measured.

In addition, samples to be measured are frequently different in the range of particle sizes, respectively, so that a problem has also occurred in the it is necessary to conduct the above-described changeover of the optical system for every different sample, and thus the measuring operation can be troublesome.

SUMMARY OF THE INVENTION

In view of the above-described conventional disadvantages, it is an object of the present invention to provide an apparatus for measuring a particle size distribution in a sample by accurately and easily measuring the particle size distribution over a wide range of particle sizes without changing the optical system.

In order to achieve the above object, an apparatus for measuring a particle size distribution wherein the particle size distribution of sample particles is determined on the basis of the theory of Fraunhofer diffraction or Mie scattering from an intensity distribution of a diffracted light or a scattered light can be obtained by means of a larger diameter particle-detecting optical system comprising laser beam-emitting device for irradiating a sample vessel, in which a medium with sample particles dispersed therein is housed, with laser beams and a ring-like detector for measuring an optical intensity of the laser beams diffracted or scattered by the sample particles at the respective scattering angles and a smaller diameter particle-detecting optical system comprising a single wavelength beam-emitting device for irradiating the sample vessel with monochrome beams obtained from a lamp light. A group of photosensors for measuring an optical intensity of the monochromated beams diffracted or scattered by the sample particles at the respective scattering angles is provided with a group of band-pass filters, in which a plurality of band-pass filters for obtaining monochrome beams different in wavelength from the lamp light are arranged. A filter-moving assembly is provided for moving the group of band-pass filters so that the respective band-pass filters may be changed within an optical path of the lamp light. The group of photosensors is arranged so as to receive the diffracted light or the scattered light from the rear of data measured by means of the ring-shaped detector and data measured by means of the group of photosensors can be taken in by means of a common data input circuit.

According to the above-described construction, an optical intensity distribution of the scattered light for a range of particle sizes having larger particle diameters is measured by means of the larger diameter particle-detecting optical system, while an optical intensity distribution of the scattered light for the range of particle sizes having smaller particle diameters is measured by means of the smaller diameter particle-detecting optical system.

In addition, in the monochrome beam-emitting device for the smaller diameter particle-detecting optical system, the single wavelength beams obtained from the lamp source light are changed over in wavelength over several stages by a movement of the group of band-pass filters by means of the filter-moving assembly so that measurements of different ranges of particle sizes are conducted for the monochrome beams having the respective wavelengths and thus the range of particle sizes, which can be measured, is expanded.

Furthermore, the group of photosensors in the smaller diameter particle-detecting optical system can receive beams having a wide range of scattering angle coming form the front of the sample vessel to the rear of the sample vessel, so that the range of particle sizes capable of being measured by the respective single wavelength beams is expanded.

Moreover, the data measured by means of the larger diameter particle-detecting optical system and the data measured by means of the smaller diameter particle-detecting optical system are taken in as data for calculating the particle size distribution by means of said common data input circuit, so that the particle size distribution over a wide range of particle sizes can be accurately measured at a single stroke without any changeover operation of the optical system.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

One preferred embodiment of the present invention is shown in FIGS. 1 to 4, in which.

Figure 5:
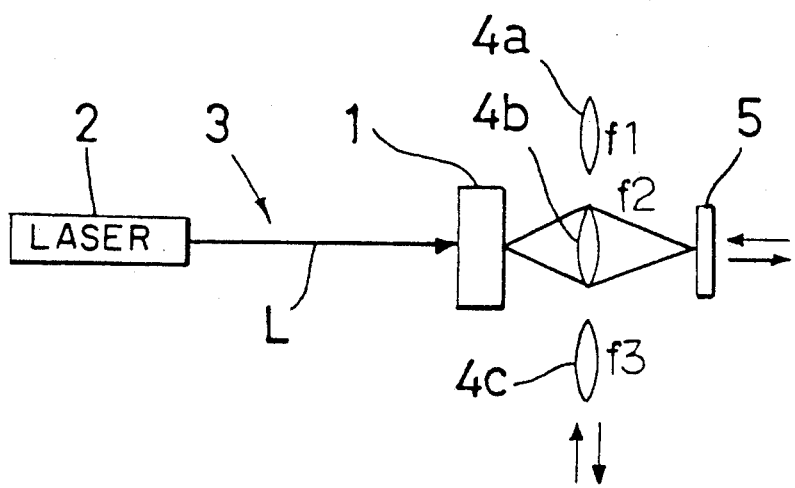
Figure 6:
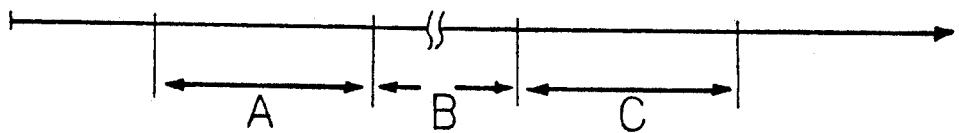

The conventional example is shown in FIGS. 5, 6, in which

FIG. 5 is a diagram showing a measuring optical system in the conventional apparatus for measuring a particle size distribution, and FIG. 6 is a diagram showing a range of particle size distribution capable of being measured by the conventional apparatus for measuring a particle size distribution shown in FIG. 5.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved apparatus for measuring particle size distribution.

The preferred embodiment of the present invention will be below described with reference to the drawings.

Figure 1:
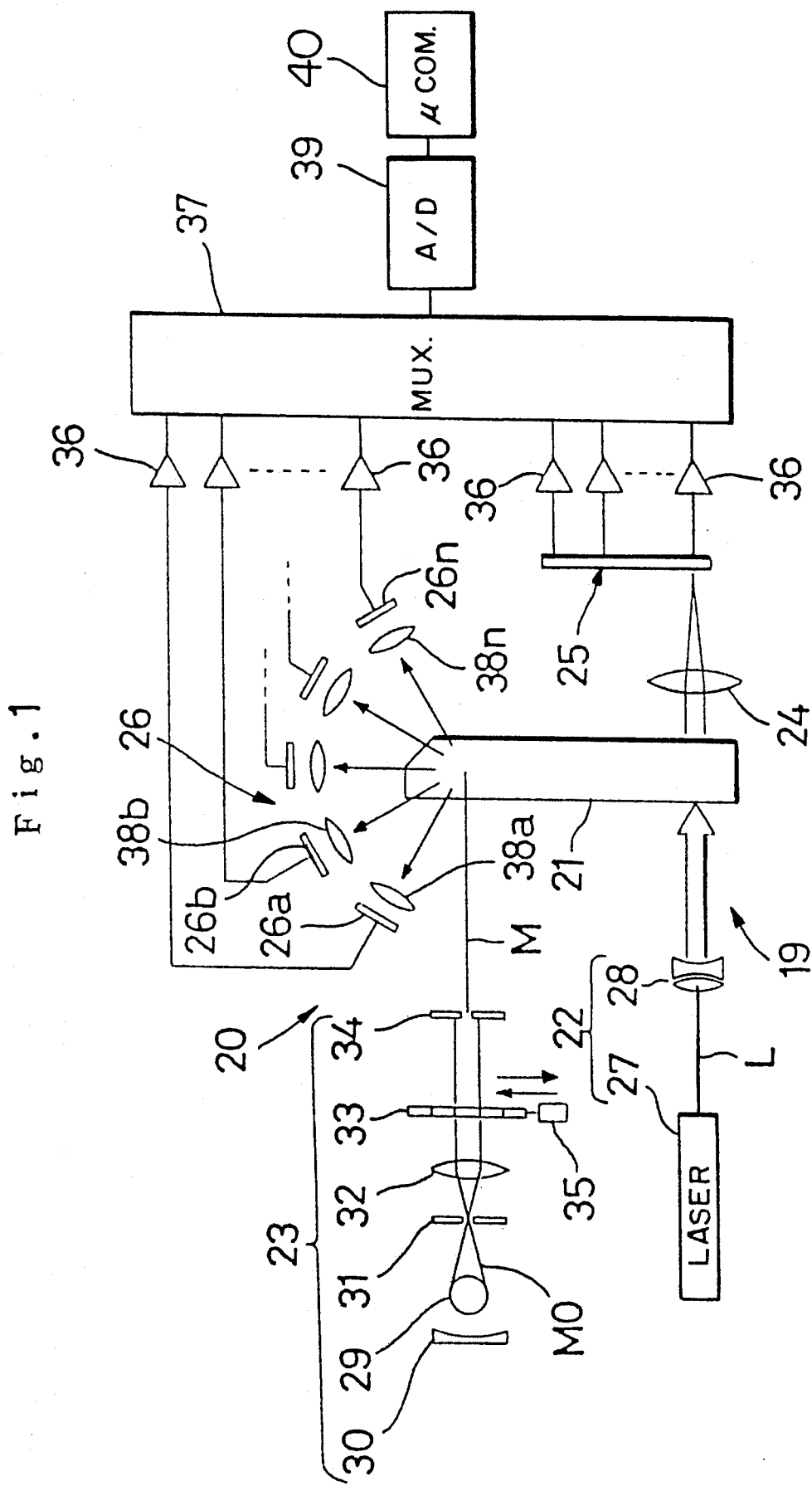
FIG. 1 is a diagram showing a measuring optical system in a apparatus for measuring a particle size distribution according to the present invention.

FIG. 1 is a schematic showing a measuring optical system in an apparatus for measuring a particle size distribution within a range of 0.04 μm to 1 mm according to the present invention. Referring to FIG. 1, a sample cell 21 is a transparent vessel, in which a sample liquid with sample particles dispersed therein is housed, and laser beam-emitting means 22 is an optical system for irradiating the sample cell 21 with parallel laser beams L. The laser beam-emitting means 22 is composed of a laser beam source 27, such as an HeNe laser having an output at 632.8 nm, for emitting parallel laser beams L, and a beam-expander lens system 28 for expanding the laser beams L into bundle of beams and the like. The laser beam inserted into the sample cell 21 has a circular diameter of approximately 5 mm. The sample call 21 has a beveled end to assist in the transmission of the laser beams at larger scattering angles.

A collecting lens 24 is arranged on an optical axis of the laser beam-emitting means 22, in front of the sample cell 21, for collecting any laser beams L diffracted or scattered by the sample particles towards a ring-shaped detector 25. The ring-shaped detector 25 is arranged in front of the collecting lens 24 for receiving those laser beams having respective scattering angles diffracted or scattered by the sample particles to measure their optical intensity distribution.

Figure 2:
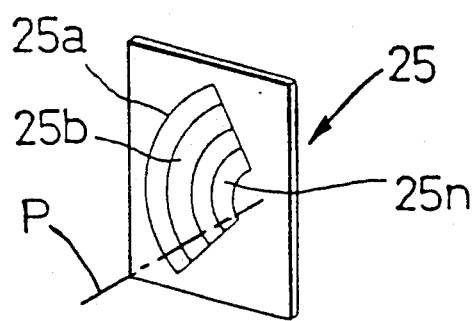
FIG. 2 is a perspective view showing a ring-shaped detector in the apparatus for measuring a particle size distribution shown in FIG. 1.

FIG. 2 is a perspective view showing a construction of the ring-shaped detector 25. The ring-shaped detector 25 is composed of a plurality of photosensors 25a, 25b, -25n arranged so as to be divided into a ring shape with the optical axis P of the laser beam-emitting means 22 as a center for detecting the laser beams L diffracted or scattered by the sample particles at respective angles depending upon particle diameters of the sample particles. The respective photosensors 25a, 25b, -25n of the ring-shaped detector 25 are connected with a multiplexer 37 through amplifiers 36 corresponding thereto. The multiplexer 37 can coordinate the inputting of the output data of each of the photosensors with the movement of the band-pass filters so that a computing system can function relative to the selected filter.

The laser beam-emitting means 22, the collecting lens 24 and the ring shaped detector 25 compose a larger diameter particle-detecting optical system 19 for receiving the laser beams diffracted or scattered by the sample particles having a relatively large particle diameters.

A single wavelength beam-emitting means 23 includes an optical system for irradiating the sample cell 21 with single wavelength beams M having wavelengths shorter than those of the laser beams L and composed of a lamp light source 29, such as a tungsten lamp, a spherical mirror 20, apparatus 31, 34, a collimator lens 32, a group of band-pass filters 33, and a filter-moving stage 35.

The spherical mirror 30 is a mirror for condensing lamp light MO emitted backward from the lamp light source 29 onto an aperture 31 arranged in front of the lamp light source 29. The aperture 31 restricts the lamp light MO from the lamp light source 29 to form a sufficiently small bundle of beams.

The collimator lens 32, arranged in front of the aperture 31, is a lens for turning the lamp light, which has been contracted by means of the aperture 31, into parallel beams. The group of band-pass filters 33, arranged in front of the collimator lens 32, is a filter for passing beams M having an appointed single wavelength from the parallel beams.

Figure 3:
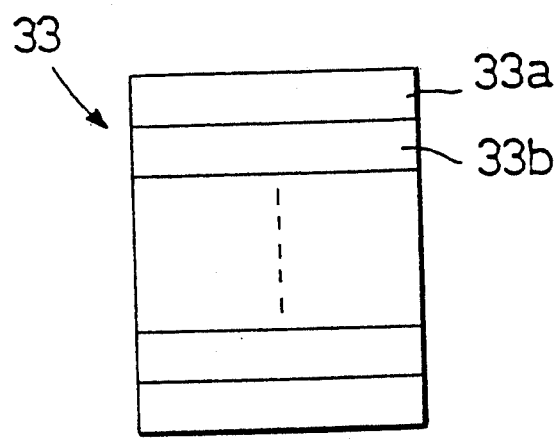
FIG. 3 is a plan view showing band-pass filters in the apparatus for measuring a particle size distribution shown in FIG. 1.

FIG. 3 is a plan view showing a construction of the group of band-pass filters 33. The group of band-pass filters 33 is composed of a plurality of ¼ wavelength plates 33a, 33b, etc., each different in transmitting a wavelength and longitudinally arranged in turn from one having a short wavelength so that the single wavelength beams may be switched over to a plurality of different wavelengths by driving the filter-moving stage 35, such as a stopper motor, to shift a position of the group of band-pass filters 33 up and down. In addition, a plurality of ¼ wavelength plates 33a, 33b, may be alternatively arranged in a ring shape so that they may be changed by rotating them by means of a filter-moving stage 35. Thus, the band-pass filters or plates are connected together for unitary movement.

The aperture 34, arranged downstream of the group of band-pass filters 33, provides a further contraction of the single wavelength beams M from the beams passing through band-pass filter 33. The single wavelength beams M, which have passed through the aperture 34, are incident upon a position different from the incident position of the laser beams L of the sample cell 21. The light beam M inserted into the sample cell 21 has a circular diameter of approximately 5 mm.

In addition, a plurality of photosensors 26a, 26b, –26n, composing a group of photosensors 26 for individually detecting the single wavelength beams M diffracted or scattered by the sample particles are arranged at the respective scattering angle positions. In particular, the photosensors 26a, 26b, –26n are arranged not only on the side in the rear of the sample cell 21, in short, the side on which the single wavelength-emitting means 23 is arranged but also on the side in the front of the sample cell 21 to measure an optical intensity for the single wavelength beams M, which are scattered ahead of the sample cell 21.

The respective photosensors 26a, 26b, –26n receive the respective diffracted or scattered beams collected by means of condensed lenses 38a, 38b, –38n corresponding thereto. The photosensors 26a, 26b, –26n are connected with the multiplexer 37 through amplifiers 36 corresponding thereto.

The single wavelength-emitting means 23, the group of photosensors 26 and the condensed lenses 38a, 38b, –38n compose a smaller diameter particle-detecting optical system 20 for receiving beams diffracted or scattered by the sample particles having relatively smaller particle diameters.

The multiplexer 37 is a circuit having a function of taking in data of the optical intensity detected by means of the photosensors 25a, 25b, –25n of the ring-shaped detector 28 and the photosensors 26a, 26b, –26n of the group of photosensors 26 in an appointed order and converting the taken-in data into series of signals in order to send them to an A/D convertor 39.

The A/D convertor 39 is a circuit for converting the data of measurement, in short, analog data, into digital data, and the digital data is sent to an operating device 40.

The operating device 40 is a device for conducting a computational operation of determining particle size distribution of the sample particles within the sample cell 21 on the basis of digital data disclosing the optical intensity. Device 40 includes a computer and appropriate software as known in the art. This operation determines the particle size distribution on the basis of an algorithm setting forth a theory of Fraunhofer diffraction or Mie scattering.

Figure 4:
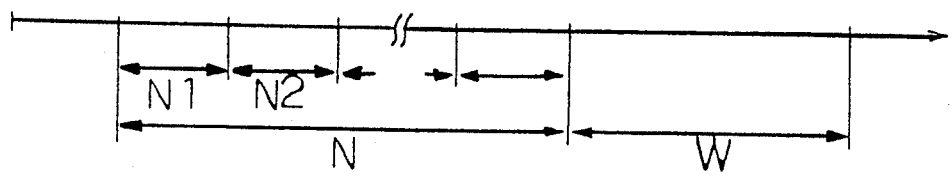
FIG. 4 is a diagram showing a range of particle size distribution capable of being measured by means of the apparatus for measuring a particle size distribution shown in FIG. 1.

FIG. 4 is a diagram schematically showing a range of the particle sizes within the particle size distribution capable of being measured by means of the above-described apparatus.

In the optical system, composing the laser beam-emitting means 22, the laser beams L from the laser light source 27 are expanded into bundle of beams by means of the beam expander 28 and then are incident upon the sample cell 21.

The laser beams L are diffracted or scattered by the sample particles within the sample cell 21 and the diffracted beams or the scattered beams are focused into an image on the ring-shaped detector 25 by means of the condensed lens 24.

An optical intensity of the laser beams L diffracted or scattered by the sample particles is measured by means of the respective photosensors 25a, 25b, –25n, arranged in the ring-like detector 25. Of the respective photosensors 25a, 25b, –25n, the photosensors on the outer circumferential side receive laser beams L scattered at larger scattering angles while the photosensors on the inner circumferential side receive the laser beams L scattered at smaller scattering angles. Accordingly, the optical intensity detected by means of the photosensors on the outer circumferential side represents a quantity of the sample particles having larger particle diameter, while the optical intensity detected by means of the photosensors on the inner circumferential side represents a quantity of the sample particles having smaller particle diameters. The optical intensities detected by means of the respective photosensors 25a, 25b, –25n are converted into analog electric signals and transmitted to the multiplexer 37 through the amplifiers 36.

On the other hand, in the optical system composing the monochrome beam-emitting means 23, the lamp light MO from the lamp light source 29 is turned into parallel beams by means of the collimator lens 32 through the aperture 31 and the parallel beams are turned into single wavelength beams M by means of the group of band-pass filters 33. In addition, the monochrome beams M are contracted into a bundle of beams by means of the aperture 4 and then are incident upon the sample cell 21.

The single wavelength beams M are diffracted or scattered by the sample particles within the sample cell 21 and the scattered beams are collected by means of the respective corresponding photosensors 26a, 26b, –26n through the respective condensed lenses 38a, 38b, –38n followed by measuring the optical intensity distribution by means of the group of photosensors 26.

In the group of photosensors 26, the photosensors arranged closer to the rear of the sample cell 21 receive the single wavelength beams M having larger scattering angles, while the photosensors arranged closer to the front of the sample cell 21 receive the monochrome beams M having smaller scattering angles. Accordingly, an optical intensity detected by means of the photosensors arranged in the rear of the sample cell 21 represents the quantity of the sample particles having smaller particle diameters, while an optical intensity detected by means of the photosensors arranged in the front of the sample cell 21 represents the quantity of the sample particles having larger particle diameters. The optical intensities detected by means of the respective photosensors 26a, 26b, –26n are converted into analog electric signals and transmitted to multiplexer 37 through the amplifiers 36. Since the wavelength range of the lamp light source 29 is previously selected so as to be shorter than the wavelength of the laser beams L, as above-described, the diffracted or scattered single wavelength beams M are effective for the determination of the particle size distribution of sample particles having smaller particle diameters. On the other hand, the diffracted or scattered laser beams L are effective for the determination of the particle size distribution of the sample particles having larger particle diameters.

Thus, the optical intensity distribution measured by means of the ring-shaped detector 25 of the larger diameter particle-detecting optical system 19 using the laser beams L having a wavelength longer than those of the lamp light MO becomes data corresponding to a range of particle sizes W having larger particle diameters shown in FIG. 4. In addition, the optical intensity distribution measured by means of the group of photosensors 26 of the smaller diameter particle-detecting optical system 20 using the lamp light MO having wavelengths shorter than those of the laser beams L becomes data corresponding to a range of particle sizes having smaller particle diameters N shown in FIG. 4.

The data of measurement, in short, analog electric signals, sent from the respective photosensors 25a, 25b, -25n, 26a, 26b, -26n are taken in the multiplexer 37 in an appointed order. That is to say, for example, the data of measurement are taken in the order from the photosensors 26a, 26b, –corresponding to the sample particles having smaller particle diameters to the photosensors 25a, 25b corresponding to the sample particles having larger particle diameters.

In addition, in the single wavelength beam-emitting means 23, the taken-out single wavelength beams M are changed in wavelength, step by step, from short wavelengths to long wavelengths every time when the position of the group of band-pass filters 33 is changed over by means of the filter-moving stage 35. As a result, also the optical intensity distribution measured by means of the group of photosensors 26 is correspondingly changed over step by step form the data corresponding to the range of particle sizes having smaller particles diameters N1 of the data corresponding to the range of particle sizes having larger particle diameters N2.

In the case where the data measured by means of the group of photosensors 26 are taken in the multiplexer 37, the taking-in cycle from the photosensor 26a to the photosensor 26n is repeated in synchronization with the changeover of the group of band-pass filters 33 by means of the filter-moving stage 35. Accordingly, the data of the ranges of particle sizes N1, N2 –ranging over several stages can be obtained as data measured by means of the smaller diameter particle-detecting optical system 20.

The analog electric signals taken in the multiplexer 37 are turned into series signals and then converted into digital signals in turn in the A/D convertor 39 and can be stored in a memory (not shown) or entered directly into the operating device 40.

In the operating device 40, the particle size distribution of the sample particles is determined on the basis of the data of the optical intensity measured by means of the ring-shaped detector 25 and the group of photosensors 26 at the respective scattering angles. This calculating procedure is conducted on the basis of the theory of the Fraunhofer diffraction or the Mie scattering.

According to the present invention, the optical intensity distribution of the scattered beams in the range of particle sizes having larger particle diameters is measured by means of the larger diameter particle-detecting optical system while the optical intensity distribution of the scattered beams in the range of particle sizes having smaller diameter particles is measured by means of the smaller diameter particle-detecting optical system, in the single wavelength beam-emitting means in the smaller diameter particle-detecting optical system the monochrome beams obtained from the lamp light being changed over in wavelength raging over several stages by the changed-over movement of the group of band-pass filters by means of the filter-moving stage, and the group of photosensors in the smaller diameter particle-detecting optical system being arranged so as to receive the beams having a wide range of scattering angles coming from the front of the sample vessel to the rear of the sample vessel, so that an effect occurs in that the particle size distribution can be measured ranging over a wide range of particle sizes.

Moreover, the data measured by means of the larger diameter particle-detecting optical system and the smaller diameter particle-detecting optical system are taken in by means of a common data input means to be used as data for calculating the particle size distribution, so that a particle size distribution ranging over a wide range of particle sizes can be accurately measured in a single measurement operation without changing over the optical system.

Those skilled in the art will appreciate that various adaptations and modifications of the just described preferred embodiment can be configured without departing from the scope and spirit of the invention. Therefore, it is to understood that, without the scope of the appended claims, the invention may be practiced other than as specifically described herein.

What is claimed is:

1. An apparatus for measuring a particle size distribution in which said particle size distribution of sample particles in a sample vessel is determined on the basis of the theory of Fraunhofer diffraction of Mie scattering from an intensity distribution of a diffracted light or a scattered light comprising:

a large diameter particle-detecting optical system including laser beam-emitting means for irradiating a sample vessel, in which a medium with sample particles dispersed therein, is housed, with laser beams and a ring-like detector for measuring an optical intensity of said laser beams diffracted or scattered by said sample particles at the respective scattering angles;

a small diameter particle-detecting optical system including monochrome beam-emitting means for irradiating said sample vessel with single wavelength beams obtained from a lamp source and a group of photosensors for measuring an optical intensity of said single wavelength beams diffracted or scattered by the sample particles at the respective scattering angles, the monochrome beam-emitting means including band-pass filter means including a plurality of band-pass filters for obtaining single wavelength beams different in wavelength from said lamp light are arranged, and filter-moving means for moving said group of band-pass filters so that said respective band-pass filters may be changed over to an optical path of the lamp light, said group of photosensors being arranged so as to receive the diffracted light or the scattered light coming from the rear of the sample vessel to the front of the sample vessel;

a common data inputting means for inputting the respective data from each photosensor and the ring-like detector, and means for determining particle size distribution from the data.

2. The invention of claim 1 wherein the band-pass filters are connected together for unitary movement into the optical path.

3. The invention of claim 1 wherein the band-pass filters are ¼ wavelength plates.

4. The invention of claim 1 wherein the common data inputting means includes a multiplexer.

5. The invention of claim 1 wherein the photosensors are also positioned on the same side of the sample vessel as the lamp source.

6. The invention of claim 5 wherein the monochrome beam-emitting means includes a plurality of condenser lens, each positioned in front of a photosensor.

7. An apparatus for measuring a particle size distribution in which said particle size distribution of sample particles in a sample vessel is determined on the basis of the theory of Fraunhofer diffraction or Mie scattering from an intensity distribution of a diffracted light or a scattered light comprising:

a large diameter particle-detecting optical system including laser beam-emitting means for irradiating a sample vessel, in which a medium with sample particles dispersed therein is housed, with laser beams and a ring-like detector for measuring an optical intensity of said laser beams diffracted or scattered by said sample particles at the respective scattering angles;

a small diameter particle-detecting optical system including monochrome beam-emitting means for irradiating said sample vessel with single wavelength beams obtained from a lamp source and a group of photosensors for measuring an optical intensity of said single wavelength beams diffracted or scattered by the sample particles at the respective scattering angles, the monochrome beam-emitting means including band-pass filter means including a plurality of band-pass filters for obtaining single wavelength beams different in wavelength from said lamp light are arranged, and filter-moving means for moving said group of band-pass filters so that said respective band-pass filters may be changed over to an optical path of the lamp light, said group of photosensors being arranged so as to receive the diffracted light or the scattered light coming from the rear of the sample vessel to the front of the sample vessel; and means, connected to outputs of the detector and photosensors, for determining particle size distribution, including a computer and a multiplexing circuit means for inputting data in coordination with the movement of the band-pass filters to the computer.

8. The invention of claim 7 wherein the band-pass filters are connected together for unitary movement into the optical path.

9. The invention of claim 7 wherein the band-pass filters are ¼ wavelength plates.

10. The invention of claim 7 wherein the photosensors are also positioned on the same side of the sample vessel as the lamp source.

11. The invention of claim 10 wherein the monochrome beam-emitting means includes a plurality of condenser lens, each positioned in front of a photosensor.

* * * * *